(12) United States Patent
Wendell et al.

(10) Patent No.: US 10,551,455 B2
(45) Date of Patent: Feb. 4, 2020

(54) MAGNETIC RESONANCE IMAGING (MRI) SYSTEMS AND METHODS USING ADIABATIC TIP-DOWN AND MATCHED ADIABATIC FLIP-BACK PULSES

(71) Applicants: Duke University, Durham, NC (US); Siemens Healthcare GmbH, Erlangen (DE)

(72) Inventors: David Wendell, Durham, NC (US); Wolfgang Rehwald, Durham, NC (US); Enn-Ling Chen, Durham, NC (US); Raymond Kim, Durham, NC (US)

(73) Assignees: Duke University, Durham, NC (US); Siemens Healthcare GmbH, Erlangen (DE)

( * ) Notice: Subject to any disclaimer, the term of this patent is extended or adjusted under 35 U.S.C. 154(b) by 124 days.

(21) Appl. No.: 15/571,633

(22) PCT Filed: May 4, 2016

(86) PCT No.: PCT/US2016/030758
§ 371 (c)(1),
(2) Date: Nov. 3, 2017

(87) PCT Pub. No.: WO2016/179264
PCT Pub. Date: Nov. 10, 2016

(65) Prior Publication Data
US 2018/0143276 A1    May 24, 2018

Related U.S. Application Data (60) Provisional application No. 62/156,389, filed on May 4, 2015.

(51) Int. Cl.
*G01V 3/00* (2006.01)
*G01R 33/46* (2006.01)
(Continued)

(52) U.S. Cl.
CPC ..... *G01R 33/4616* (2013.01); *G01R 33/3614* (2013.01); *G01R 33/446* (2013.01);
(Continued)

(58) Field of Classification Search
CPC .............. G01R 33/543; G01R 33/5612; G01R 33/3607; G01R 33/5659; G01R 33/583
(Continued)

(56) References Cited

U.S. PATENT DOCUMENTS

| 6,285,900 | B1 * | 9/2001 | Stuber | G01R 33/446 |
| | | | | 324/306 |
| 2006/0080044 | A1 * | 4/2006 | Ropele | G01R 33/563 |
| | | | | 702/23 |

(Continued)

FOREIGN PATENT DOCUMENTS

| JP | 2003-033332 A | 2/2003 |
| WO | 05-176909 A | 7/1993 |

(Continued)

OTHER PUBLICATIONS

International Search Report and Written Opinion issued in PCT Application No. PCT/US2016/030758 dated Aug. 30, 2016.

(Continued)

*Primary Examiner* — Walter L Lindsay, Jr.
*Assistant Examiner* — Frederick Wenderoth
(74) *Attorney, Agent, or Firm* — Olive Law Group, PLLC (57) ABSTRACT

Magnetic resonance imaging (MRI) systems and methods using adiabatic tip-down and matched adiabatic flip-back pulses are disclosed. According to an aspect, a system includes a signal generator configured to generate a pulse sequence for on-resonance magnetization transfer preparation. The pulse sequence includes an adiabatic tip-down pulse and a matched adiabatic flip-back pulse for separating spins in a mobile spin pool from spins in a bound spin pool (Continued)

of an anatomical region of interest for imaging. The system includes radio frequency (RF) coils configured to transmit RF pulses in response to the pulse sequence and to acquire RF data in response to transmission of the RF pulses. Further, the system includes a processing system configured to process the RF data to provide a display image indicating different tissue types with discrimination.

36 Claims, 6 Drawing Sheets

(51) Int. Cl.
  *G01R 33/56* (2006.01)
  *G01R 33/36* (2006.01)
  *G01R 33/44* (2006.01)
  *G01R 33/483* (2006.01)
  *A61B 5/055* (2006.01)

(52) U.S. Cl.
  CPC ..... *G01R 33/4838* (2013.01); *G01R 33/5605* (2013.01); *G01R 33/5607* (2013.01); *A61B 5/055* (2013.01)

(58) Field of Classification Search
  USPC ........................................ 324/314
  See application file for complete search history.

(56) References Cited

U.S. PATENT DOCUMENTS

| | | | |
|---|---|---|---|
| 2006/0284615 A1* | 12/2006 | Nazafat | G01R 33/5635 324/307 |
| 2012/0194186 A1* | 8/2012 | Rehwald | G01R 33/50 324/309 |
| 2014/0002077 A1 | 1/2014 | Deshpande et al. | |
| 2014/0035580 A1* | 2/2014 | Andronesi | G01R 33/36 324/309 |
| 2015/0005645 A1* | 1/2015 | Thompson | A61B 5/7235 600/479 |
| 2015/0042336 A1* | 2/2015 | Feiweier | G01R 33/4833 324/309 |

FOREIGN PATENT DOCUMENTS

| | | |
|---|---|---|
| WO | 02/44746 A2 | 6/2002 |
| WO | 03-063912 A1 | 8/2003 |

OTHER PUBLICATIONS

International Preliminary Report on Patentability issued in counterpart PCT Application No. PCT/US2016/030758 dated Nov. 7, 2017 (six (6) pages).

* cited by examiner

MAGNETIC RESONANCE IMAGING (MRI) SYSTEMS AND METHODS USING ADIABATIC TIP-DOWN AND MATCHED ADIABATIC FLIP-BACK PULSES

CROSS REFERENCE TO RELATED APPLICATION

This is a 371 national stage patent application, which claims priority to PCT International Patent Application No. PCT/US2016/030758, filed May 4, 2016, and titled MAGNETIC RESONANCE IMAGING (MRI) SYSTEMS AND METHODS USING ADIABATIC TIP-DOWN AND MATCHED ADIABATIC FLIP-BACK PULSES, which claims the benefit of U.S. Provisional Patent Application No. 62/156,389, filed May 4, 2015, and titled METHODS AND APPARATUS FOR ON-RESONANCE MAGNETIZATION TRANSFER (MT) PREPARATION USING TIME DELAY-SEPARATED MATCHED PAIRS OF ADIABATIC PULSES, the disclosures of which are incorporated herein by reference in its entirety their entireties.

TECHNICAL FIELD

The present subject matter relates to magnetic resonance imaging (MRI). More particularly, the present subject matter relates to MRI systems and methods using adiabatic tip-down and matched adiabatic flip-back pulses.

BACKGROUND

Radiology is a medical specialty that uses imaging to diagnose and treat diseases within a patient. A commonly used imaging technique is magnetic resonance imaging (MRI). MM scanners use strong magnetic fields, radio waves, and field gradients to form images of a patient. One technique used in MRI involves magnetization transfer (MT), which takes advantage of cross-relaxation between hydrogen nuclei in macromolecules and those in water. A simple model can be employed to explain the magnetization transfer (MT) effect. Magnetic spins can be classified into two pools. One pool contains free, mobile spins observable by MM, the other pool bound, restricted, not directly observable spins. Matter with a high macromolecular content such as tissue contains mainly bound, restricted spins. These spins have very short T2 values on the order of microseconds, rendering them invisible with conventional MRI. The application of RF energy to the macromolecular pool results in a some degree of saturation of the free water pool. The extent of the saturation of the free water pool depends on the coupling between the macromolecular pool and the free water pool, and can provide unique insights into tissue structure and composition. There is a continuing need to provide improved MRI systems and techniques for taking advantage of magnetization transfer.

SUMMARY

Disclosed herein are MRI systems and methods using adiabatic tip-down and matched adiabatic flip-back pulses. According to an aspect, a system includes a signal generator configured to generate a pulse sequence for on-resonance magnetization transfer preparation. The pulse sequence includes an adiabatic tip-down pulse and a matched adiabatic flip-back pulse for separating spins in a mobile spin pool from spins in a bound spin pool of an anatomical region of interest for imaging. The system includes radio frequency (RF) coils configured to transmit RF pulses in response to the pulse sequence and to acquire RF data in response to transmission of the RF pulses. Further, the system includes a processing system configured to process the RF data to provide a display image indicating different tissue types with discrimination.

BRIEF DESCRIPTION OF THE DRAWINGS

The foregoing aspects and other features of the present subject matter are explained in the following description, taken in connection with the accompanying drawings, wherein.

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

In this disclosure, "comprises," "comprising," "containing" and "having" and the like can have the meaning ascribed to them iii U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "about" is understood as within a range of normal tolerance in the art, for example within 2 standard deviations of the mean. The term "about" can be understood as within 10%, 9%, 8%, 7%, 6%, 5% 4%, 3%, 2%, 1%, 0.5%, 0.1%, 0.05%, or 0.01% of the stated value. Unless otherwise clear from context, all numerical values provided herein are modified by the term "about."

Unless otherwise defined, all technical terms used herein have the same meaning as commonly understood by one of ordinary skill in the art to which this disclosure belongs.

The presently disclosed subject matter relates to MRI involving pulsed on-resonance magnetization transfer (MT) preparations. The individual MT preparations are robust to phase dispersions produced by poor magnetic field homogeneity. Presently disclosed systems and methods provide separation of tissues based on the concentration of hydrogen nuclei (spins) bonded to macromolecules compared with those comprising water. MT contrast is generated by selectively saturating the portion of the MRI frequency spectrum due to spins attached to macromolecules. The spins associated with macromolecules have very short T2 values (microseconds) compared to spins in free water. After the application of the tip-down pulse, the magnetization is in the transverse plane. Magnetization of the restricted spins decays quickly due to their short T2, while the free water spins are largely unaffected. In the solid matter, energy is then transferred from the free spins to the restricted spins. This is known as the MT effect, which causes overall reduction of magnetization of the solid matter, for example in myocardium. The flip-back pulse returns, the transverse magnetization to the longitudinal direction. During the following time delay, further energy exchange by MT takes place. The magnetization differences are now stored as longitudinal magnetization. The magnitude of the reduction in MRI signal is proportional to the macromolecular content of the tissue. For example, fluids have very little MT effect so magnetization is largely unaffected. The module can be played in isolation or repeated to accentuate the difference in magnetization between solid matter and fluid. This reduces tissue signal more than blood signal and creates image contrast between tissue and blood. Any remaining transverse magnetization at the end of the preparation block is spoiled. The presently disclosed systems and methods can use pulses which compensate for imperfections within the pulse itself, and are robust to variations in B0 and B1 within the scanner. These pulses are kept as short as possible to reduce contamination of MT contrast by magnetization weighting during the pulse application itself. By keeping the pulse short, contamination can be limited and the majority of contrast is created by the MT effect described above. The presently disclosed subject matter can be applied to morphological MR imaging where it increases tissue blood contrast. It can be used to accentuate the difference in water content between different tissue types. Further, it can be combined with a trailing inversion recovery pulse to create dark blood delayed enhancement images. It can be used for MR angiography where it reduces the background tissue signal while keeping the blood bright. It can be combined with any data readout.

Figure 1:
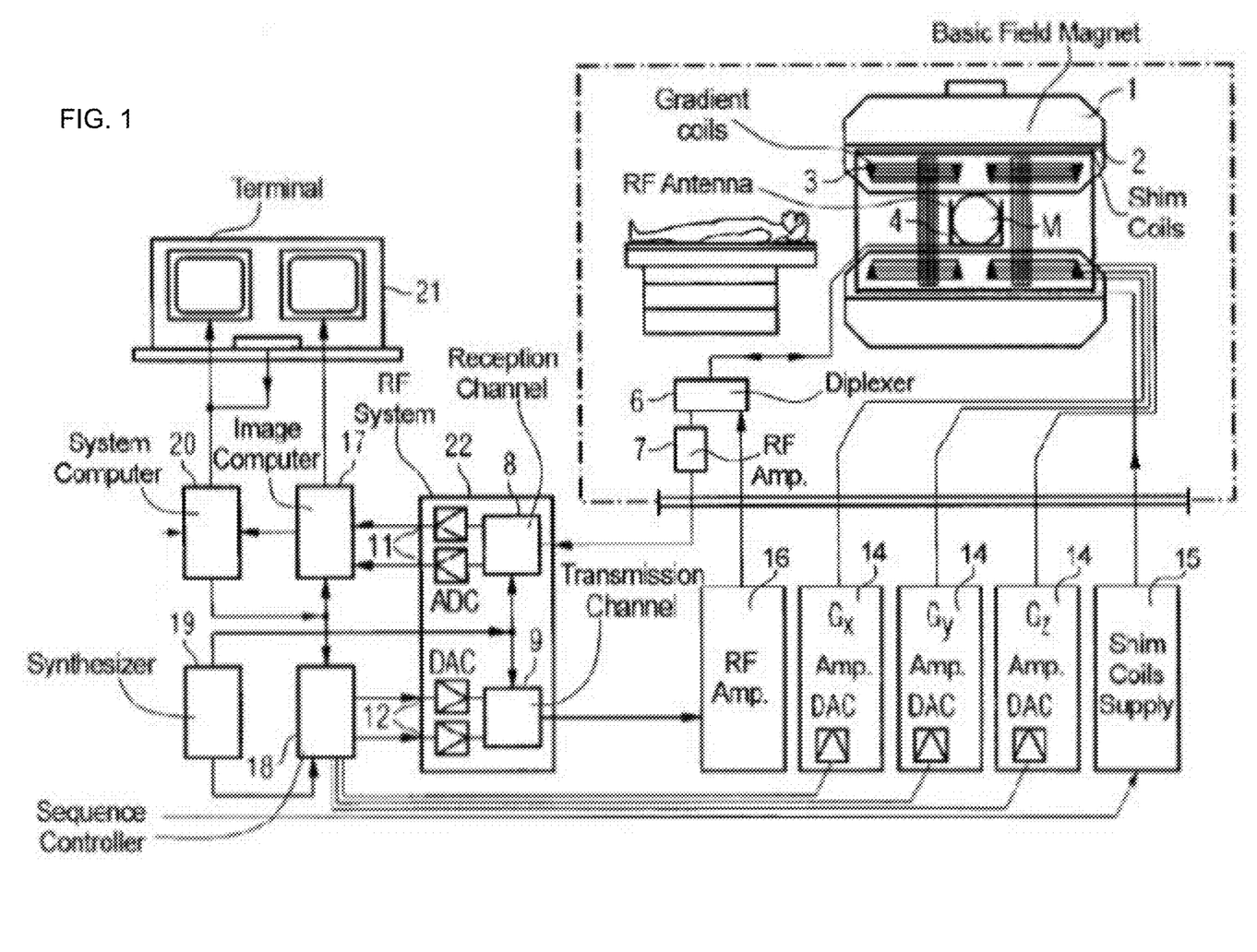
FIG. 1 is a diagram of an example MRI system for discriminating between imaged tissue type in accordance with embodiments of the present disclosure.

FIG. 1 illustrates a diagram of an example MRI system for discriminating between imaged tissue type in accordance with embodiments of the present disclosure. Referring to FIG. 1, RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17. Imaging computer 17 reconstructs an image from the processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined frequency, phase and amplitude times, transmission of RF pulses with a determined frequency, phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens.

A signal generator (sequence controller 18) generates a pulse sequence for on-resonance magnetization transfer preparation. The pulse sequence can include a series of an adiabatic tip-down pulses and matched adiabatic flip-back pulses for separating spins in a mobile spin pool from spins in a bound spin pool of an anatomical region of interest for imaging. RF coils 4 can transmit RF pulses in response to the pulse sequence and to acquire RF data in response to transmission of the RF pulses. A processing system (imaging computer 17) can process the RF data to provide a display image indicating different tissue types with discrimination.

A basic field magnet 1 can generate a strong magnetic field, which is constant in time, for the polarization or alignment of the nuclear spins in the examination region of an object, such as, for example, a part of a human body to be examined. The high homogeneity of the basic magnetic field required for the magnetic resonance measurement is provided in a spherical measurement volume M, for example, into which the parts of the human body to be examined are brought. In order to satisfy the homogeneity requirements and especially for the elimination of time-invariant influences, shim-plates made of ferromagnetic material are mounted at suitable positions. Time-variable influences may be eliminated by shim coils 2, which can be controlled by a shim-current supply 15.

In the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by the sequence controller 18 for the generation of gradient pulses at proper times.

Within the gradient field system 3, radio-frequency (RF) coils 4 are located which converts the radio-frequency pulses emitted by a radio-frequency power amplifier 16 via multiplexer 6 into a magnetic alternating field in order to excite the nuclei and align the nuclear spins of the object to be examined or the region of the object to be examined. RF coils 4 may include a subset or substantially all of, multiple RF coils arranged in sections along the length of volume M corresponding to the length of a patient. Further, an individual section RF coil of coils 4 may include multiple RF coils providing RF image data that is used in parallel to generate a single MR image. RF pulse signals can be applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via an amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In a transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M. The conversion from transmitting to receiving operation is done via a multiplexer 6. System computer 20 automatically (or in response to user command entered via terminal 21) determines pulse sequence timing parameters for discriminating between MR imaged tissue type based on magnetization transfer.

Figure 2A:
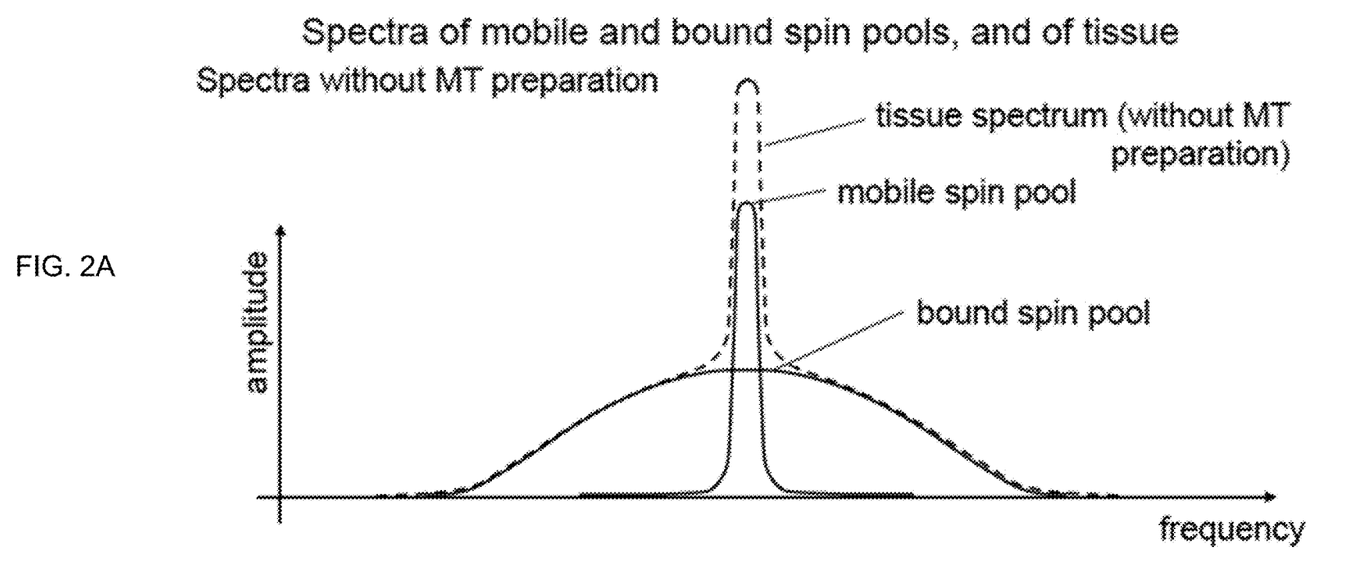
FIGS. 2A and 2B are graphs showing spectra of mobile and bound spin pools, and of tissues.

To understand the effect of magnetic preparations on the two spin pools, in some cases it is simpler to consider the T2-decay in the time domain, in other cases the spectra in the frequency domain. Generally, a rapid signal decay in the time domain corresponds to a broad spectrum in the frequency domain, and a slow decay in the time domain to a narrow peak in the frequency domain. It is noted that restricted spins have very short T2 values on the order of microseconds, and consequently can be invisible with conventional MM. Their very fast exponential decay in the time domain corresponds to their very wide spectrum in the frequency domain, as shown in the example of FIG. 2A. The transverse decay of the mobile (free water) spins is slow (T2 is long) and corresponds to a very narrow peak in the frequency domain, also shown in FIG. 2A. Tissue such as myocardium is a mixture of bound and mobile spins and is therefore a superposition of both fast and slow decay, seen as dashed line spectrum in FIG. 2A.

Figure 2B:
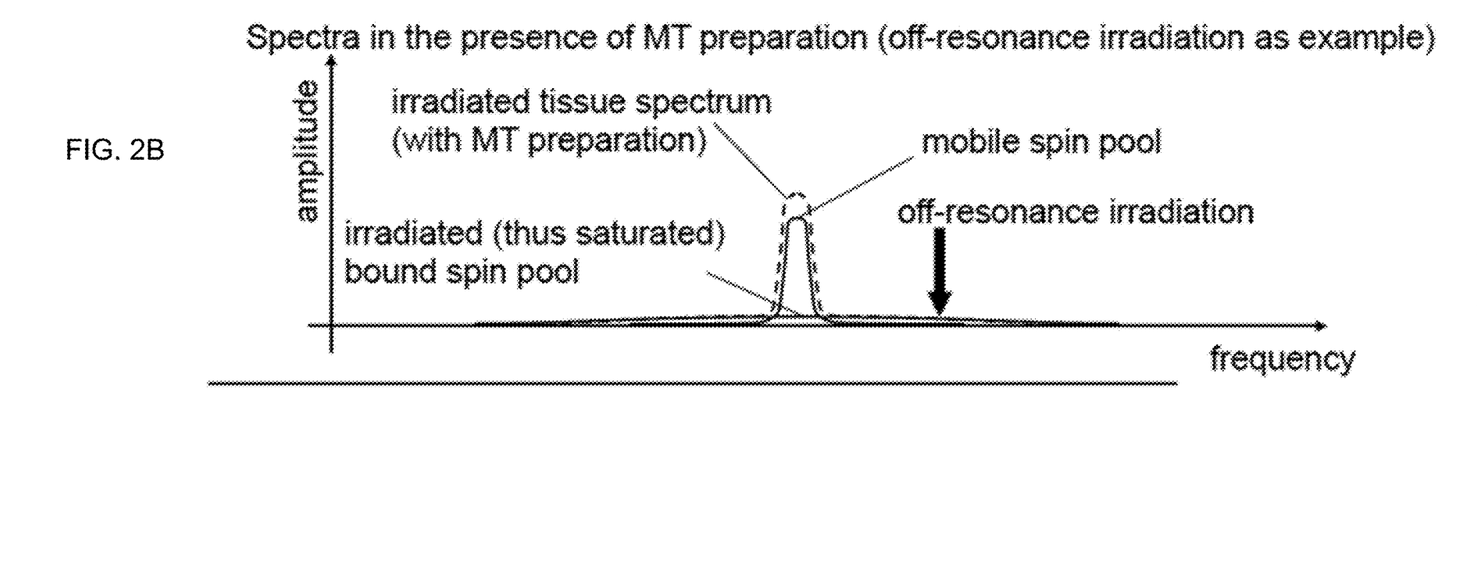

If the magnetization of the bound spins in tissue is selectively irradiated off-resonance RF (see thick down-pointing arrow in FIG. 2B), the bound spin pool becomes saturated (low signal) as shown in FIG. 2B. Subsequently, magnetization transfers from the tissue's mobile spin pool to its restricted spin spool via cross-relaxation, dipole-dipole interactions, and exchange hydrogen species, resulting in a reduced mobile spin magnetization. The observed overall tissue magnetization is thus reduced as seen by the dashed spectrum in FIG. 2B. Due to this magnetization transfer from one spin species to the other, otherwise unobservable bound spins can be indirectly imaged by their effect on the free, visible spins. The created image contrast is known as MT contrast. Importantly, whereas the vastly different T2 values of the two spin pools are responsible for the different initial magnetization of the pool, the observed image contrast is not to be confused with T2-weighting. Rather, image contrast is a function of the magnetization transfer between these pools and the ratio of these pools in each imaged voxel.

The selective saturation of bound spins can be achieved by three methods:

(1) A low-intensity, off-resonance (off Larmor frequency) continuous wave (CW) irradiation can be applied to a specimen or patient. Due to its off-resonance property, only the bound spin pool with its wide spectrum is saturated. Concurrently with this saturation, magnetization is transferred from the mobile to the bound spin pool so that the magnetization of the mobile pool is indirectly reduced via the MT effect.

(2) The CW off-resonance irradiation can be replaced with off-resonance pulses of a very large flip angle. Again, only the bound spin pool with its wide spectrum is directly saturated. One or a series of these pulses can be applied. This is known a "pulsed off-resonance MT" preparation and may be used for MT preparation on clinical MRI scanners.

(3) A binomial or adiabatic zero-degree pulse or pulse series can be played at the mobile spin resonance. This acts as T2 filter by saturating short T2 species while hardly affecting long T2 species. This method directly affects the bound pool, indirectly the mobile pool. It is known as "pulsed on-resonance MT". The presently disclosed systems and methods may be implemented in accordance with this technique.

In cardiovascular Mill, separating myocardium from blood is of major importance. Blood mainly consists of mobile spins and is therefore largely unaffected by any MT preparation. Myocardium contains mostly bound spins and much fewer mobile spins. The myocardial MR signal is therefore significantly reduced by MT preparation.

In accordance with embodiments, the presently disclosed subject matter may be used for pulsed on-resonance magnetization transfer (MT) preparations. In an example, an MRI system may generate a pair of matched adiabatic 90 degrees radio frequency (RF) pulses, specifically an adiabatic tip-down followed by a first time delay, and a matched adiabatic flip-back RF pulse followed by a second time delay. The phase and amplitude modulation function of the flip-back pulse can be matched to those of the tip-down pulse. Matching can be achieved by playing the flip-back modulation functions (the amplitude and the phase modulation function) time-reversed (mirrored in time) relative to the tip-down functions. Any phase dispersion created by the tip-down pulse is thus compensated by the flip-back pulse. The preparation has very homogeneous image quality due to this compensation mechanism and due to the use of adiabatic RF pulses that are intrinsically B1 and B0 insensitive. The first time delay is in the range of 10 µs to 10 ms, and it can control the separation between different T2-species. The second time delay is in the range of 1 ms to 500 ms. Both time delays affect the magnetization transfer between free and restricted spins as described further herein.

In accordance with this embodiment, the presently disclosed systems and methods can reduce the magnetization of solid matter, which typically has a high macromolecular content (for example myocardial tissue), to a larger extent than the magnetization of fluids, which typically contain fewer macromolecules (for example blood or effusion). Solid matter contains more restricted spins that have very short T2 values on the order of microseconds. Fluids contain mainly free spins that have very long T2 values on the order of milliseconds to seconds. During the first time delay the magnetization of restricted spins in solid matter decays rapidly due to their short T2. The magnetization of free spins in solid matter and fluids is largely unaffected. During said second time delay, the magnetization in the solid matter is transferred from the free spins to the restricted spins, which is commonly known as MT effect and which causes an overall reduction of magnetization of the solid matter. Fluids have very little MT effect so their magnetization is substantially unaffected.

In accordance with embodiments, the presently disclosed systems and methods can generate matched pulses and time delays, or of multiple such modules played in series. The larger the number of modules, the more signal separation between fluid and solid matter is achieved. The present disclosure can reduce tissue signal more than blood signal, and thereby create image contrast between tissue and blood. A trailing spoiling gradient for destruction of all remaining transverse magnetization can be played after the last module in the series.

Systems and methods described herein may advantageously make use of adiabatic paired 90-degrees pulses that are matched with each other to compensate pulse imperfections. The adiabatic nature of these pulses acts to achieve optimal B0 and B1 performance. The adiabatic pulse shape used for reduction to practice is a tan/tan h modulation (known as a hyperbolic tangent pulse), because it can be played as a short duration pulse (maximum duration 7 ms) due to its low peak power. Other suitable adiabatic pulse shapes may also be used, as long as the tip-down and flip-back are matched according to the present disclosure, and as long as they can be played in a relatively short time. Short pulse duration is important since the spin lock regime during the application of any adiabatic pulse creates magnetization weighting which depends on T1, T2, and the specific parameters of the pulse. This contaminates the pure MT contrast that the module aims to create. By keeping the pulses short, contamination is limited and the main contrast created by systems and methods disclosed herein is MT contrast.

It is noted that systems and methods of the present disclosure can be applied to morphological MR imaging where it increases tissue blood contrast. It can be used to accentuate the difference in water content between different tissue types. It can be combined with a trailing inversion recovery pulse to create dark blood delayed enhancement images with FIDDLE-like (Flow Independent Dark blood DeLayed Enhancement) contrast. It can be used for MR angiography where it reduces the background tissue signal while keeping the blood bright. In addition, it can be combined with any data readout.

Presently disclosed systems and methods can create MT contrast through a brief time delay between matched tip-down and flip-back pulses, and a brief time delay after the flip-back pulse. This requires lower energy, SAR, and power than adiabatic zero-degree pulses and provides an improvement. For a given energy, the achieved MT weighting is much stronger than off-resonance MT techniques making it highly efficient. It is also more efficient than a binomial zero degree pulse that only has a minimal time delay between its components thus providing no significant MT effect. Due to the reduced energy and average power demands of the present subject matter, multiple of the tip-down flip-back modules can be played to increase its MT effect, which is already stronger than in the prior art, without exceeding energy, power, and SAR limits.

In accordance with embodiments, presently disclosed systems and methods use a flip-back amplitude and phase modulation function that is time-reversed relative to the tip-down function. Any phase dispersion created by the tip-down pulse is thus compensated by the flip-back pulse. Due to this compensation mechanism, the preparation has very homogeneous image quality. Also, the presently disclosed subject matter uses adiabatic RF pulses that are intrinsically B1 and B0 insensitive provides for a homogeneous preparation. The image quality is superior to that obtained by binomial zero-degree pulses.

Unlike some adiabatic zero-degree pulses, the amount of MT weighting can be adjusted by modifying the time delays between the tip-down and flip-back pulse and after the flip-back pulse, without modifying the adiabatic pulses themselves. A larger delay between the pulses creates a larger separation of the short T2-decay curves of the bound spins from the long T2-decay curves of the mobile spins. This mechanism indirectly controls the magnetization transfer within the tissue or solid matter. An example working range for the time delay can be between about 10 µs and about 10 ms. In the myocardium, a time delay of about 500 µs can be a good compromise between sufficient MT weighting and adequate motion- and B0-robustness. Long delay times can cause inhomogeneity due to T2*-dephasing. In the prior art of "adiabatic zero-degree pulses" such control is not possible. In some previous efforts, one can only modify the duration of the pulse, which affects its bandwidth and its T2/T1 weighting, and not just its MT weighting. Therefore, previous efforts do not possess a parameter that exclusively controls the effect on mobile and bound spin pool, whereas systems and methods according to the presently disclosed subject matter does. The second time delay directly affects the magnetization transfer between free and restricted spins. A longer delay allows more MT to take place. The delay may typically be in the range of 1 ms to 500 ms. Like the first time delay, this second delay also only affects a single parameter related to MT-weighting, and makes for an uncontaminated MT contrast.

Despite the adiabatic nature of the pulses in the invention, the magnetic spins spend less time in the spin-lock regime compared to the adiabatic zero-degree pulses. The time delays are the main determinant of the invention's MT image contrast. Therefore, the presently disclosed subject matter can produce MT contrast with less contamination by T2/T1 contrast than the other on-resonance methods.

In summary, the presently disclosed subject matter can create a stronger, more homogeneous and less contaminated MT contrast than other known on-resonance methods. For the same amount of MT effect, it is much more energy-efficient than the known off-resonance methods.

The following provides some example implementations of the presently disclosed MT preparation using time delay-separated matched pairs of adiabatic pulses based on the key ideas disclosed above.

Figure 3:
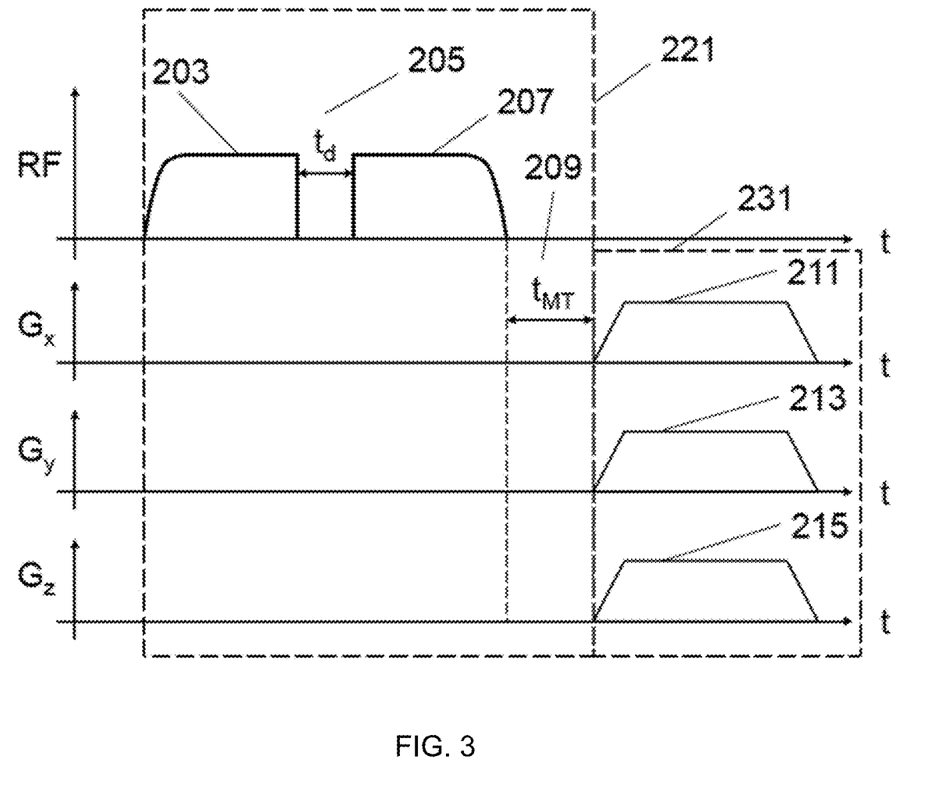
FIG. 3 shows a single on-resonance MT preparation module according to invention principles.

FIG. 3 depicts a single on-resonance MT preparation module in accordance with embodiments of the present disclosure. The adiabatic tip down pulse 203 brings all magnetization into the transverse plane. This is a 90 degree adiabatic pulse that can be tan/tan h modulated. Other energy- and power-efficient short adiabatic RF pulses (up to 7 ms) can be used. During the time delay 205 $t_d$ transverse magnetization decays according to the T2 values of the prepared spin pools in tissue and fluids. Bound spins have very short T2 values and their signal thus decays rapidly, within microseconds to a few milliseconds. Mobile spins have very long T2 values on the order of hundreds of milliseconds to seconds and they are hardly affected during time delay 205 $t_d$. The matched adiabatic flip back pulse 207, a −90 degrees RF pulse, returns all magnetization to the longitudinal direction. It is an important concept of the present disclosure that the amplitude and phase modulation functions of flip back pulse 207 are time-reversed relative to the respective functions of tip-down pulse 203. Owing to this concept of pulse matching any phase dispersion created by tip-down pulse 203 is corrected by the flip-back pulse. The flip-back pulse 207 is followed by time delay $t_{MT}$ during which magnetization transfer occurs. Pulses 203, 207 and time delays 205, 209 form a module 221. Module 221 can be repeated multiple times. The last event in the module is spoiling block 231, which contains the application of spoiling gradients 211, 213, 215 on the x-, y-, and z-axis, respectively. This destroys all remaining transverse magnetization. Different spoiling blocks may be used, for example a spoiling gradient can only be applied on one axis. Also, random and rotating amplitude and sign of the spoiling gradients is possible.

Figure 4:
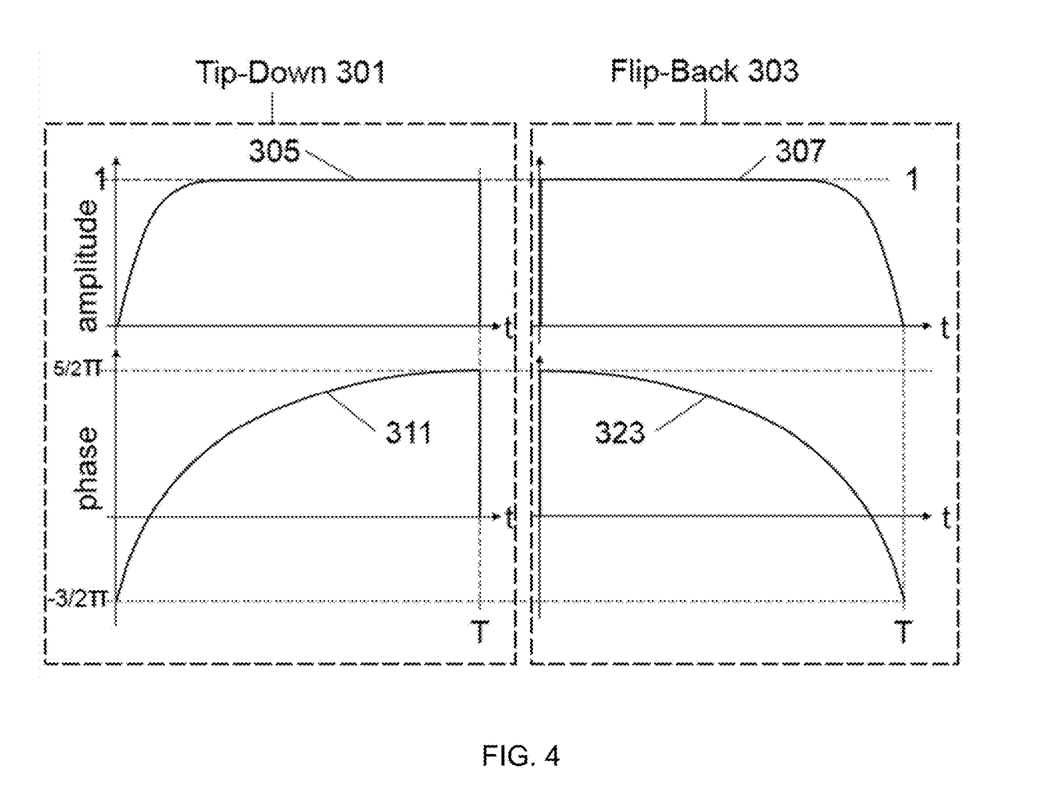
FIG. 4 depicts a graph showing exemplary amplitude and phase modulation functions of the tip-down and the flip-back pulse within a single on-resonance MT preparation module in accordance with embodiments of the present disclosure.

FIG. 4 depicts a graph showing exemplary amplitude and phase modulation functions of the tip-down 301 and the flip-back pulse 303. The amplitude modulation 307 of the flip-back pulse equals the time-reversed amplitude modulation 305 of the tip-down pulse. The phase modulation 323 of the flip-back pulse equals the time-reversed phase modulation 311 of the tip-down pulse. This example uses a tan/tan h modulated adiabatic half passage for each pulse, according to the following equations:

$$\text{amplitude}_{tip\text{-}down}\text{: } \omega_{1,tip\text{-}down}(t) = \omega_{1max}\tanh\left[\zeta\left(\frac{t}{T}-1\right)\right]$$

$$\text{phase}_{tip\text{-}down}\text{: } \Phi_{tip\text{-}down}(t) = \frac{\Phi_{max}}{4} - \frac{\Delta\omega_{max}\cdot T}{\kappa\tan\kappa}\cdot\ln\left[\frac{\cos\left(\kappa\left(\frac{t}{T}-2\right)\right)}{\cos\kappa}\right]$$

with 0<t<T and pulse duration T, peak pulse amplitude $\omega_{1,max}$, frequency sweep $\omega_{1max}$, and constants $\zeta$ and K.

The corresponding flip-back pulse functions are:

$$\omega_{1,flip\text{-}back}(t)=\omega_{1,tip\text{-}down}(T-t)$$

$$\Phi_{flip\text{-}back}(t)=\Phi_{tip\text{-}down}(T-t)$$

Other modulation functions can also be used, as long as above time-reversal relationship between tip-down and flip back is fulfilled. Therefore, the presently disclosed subject matter may not be limited to a single adiabatic waveform.

Figure 5:
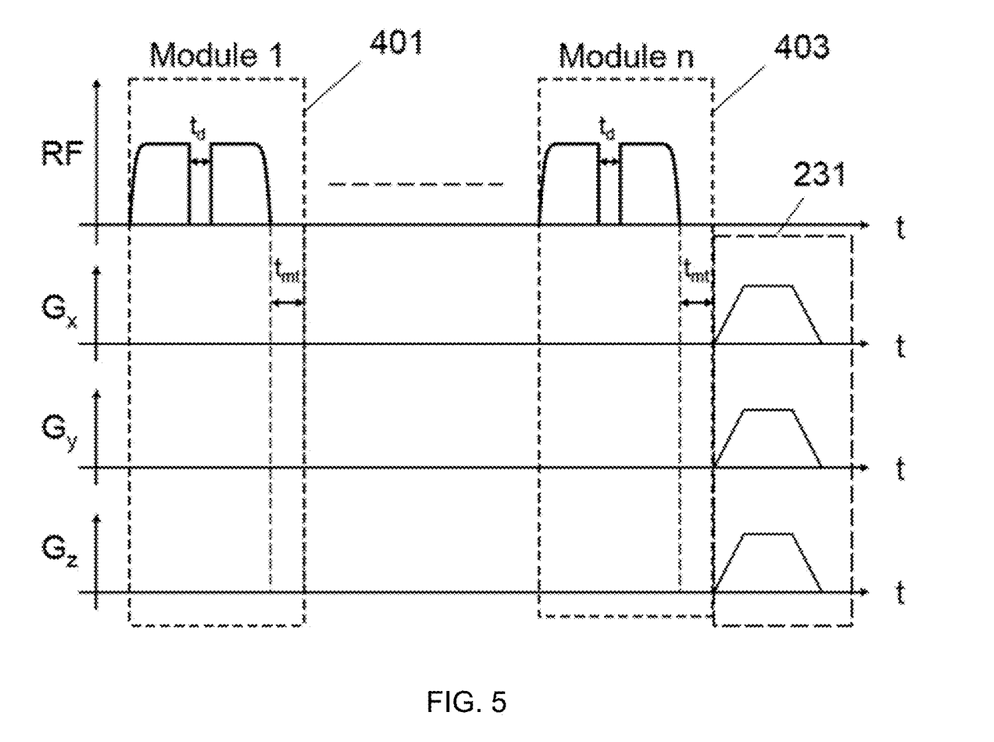
FIG. 5 illustrates a graph depicting embodiments including a series of n matched pulse modules from FIG. 3.

FIG. 5 illustrates a graph depicting embodiments including a series of n matched pulse modules 221 from FIG. 3. Module 1 (401) and module n (403) are the first and last in a module series, respectively. The larger the number of modules n, the more separation between fluid and solid matter is achieved. The series is followed by spoiling event 231 according to FIG. 3.

Figure 6:
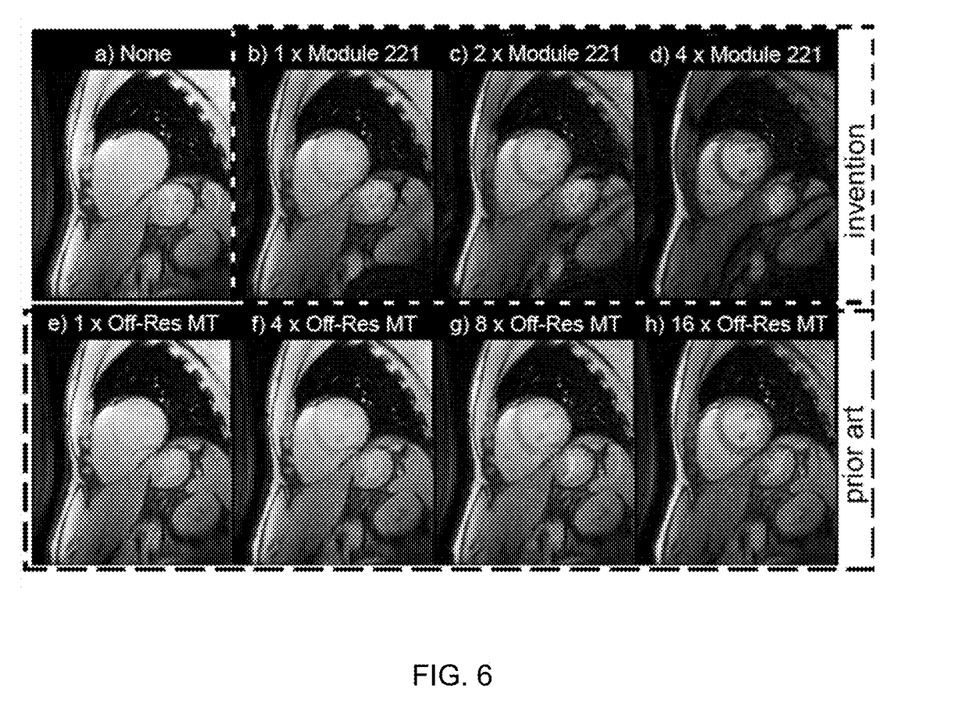
FIG. 6 shows MR images acquired with no prep (panel a), with the invention (panels b-d) in accordance with embodiments of the present subject matter, and with a prior art method (panel e-h).

FIG. 6 shows MR images acquired with no prep (a), in accordance with embodiments of the present subject matter (b-d), and with a prior art method (e-h). Panel (a) shows a standard gradient echo image of the heart acquired in the short-axis orientation. The image contrast between blood pool and myocardium is poor. Panel (b) shows the same view acquired with exactly the same gradient echo readout, but one module (n=1) of matched pulsed pairs 221 followed by spoiler block 231, according to principles of the present disclosure was applied prior readout. Image contrast between blood and myocardium is improved. Due to the MT contrast generated myocardial signal is reduced without much affecting blood signal. For panel (c) 2 modules (n=2) of matched pulse pairs 221 are played creating a stronger contrast than in (b). For panel (d) 4 modules (n=4) of matched pulse pairs 221 are played resulting in an even stronger MT contrast. The MT effect of the present disclosure was compared to prior art using an increasing series of Gaussian off-resonance MT pulses and the same gradient echo readout (FIG. 6 (e)-(h)). Panel (e) uses one pulse and achieves very little MT weighting, panel (f) 4 pulses, panel (g) 8 pulses and panel H 16 pulses. The comparison of present subject matter and prior art, specifically of (b) with (f), (c) with (g), and (d) with (h) reveals the much stronger myocardium to blood contrast achieved by the presently disclosed subject matter despite using a smaller number of the invented modules compared to the Gaussian off-resonance pulses.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs may be implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims. One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

REFERENCES

1. Hua, J. and G. C. Hurst, *Analysis of on-and off-resonance magnetization transfer techniques.* Journal of Magnetic Resonance Imaging, 1995. 5(1): p. 113-120.
2. Kim, R. J., *Blood signal suppressed contrast enhanced magnetic resonance imaging.* 2012, Google Patents.
3. Balaban, R. S., *Magnetization Transfer between Water and Macromolecules in Proton MRI,* in *eMagRes.* 2007, John Wiley & Sons, Ltd.
4. Taheri, S. and R. Sood, *Spin-lock MRI with amplitude-and phase-modulated adiabatic waveforms: an MR simulation study.* Magnetic Resonance Imaging, 2006. 24(1): p. 51-59.
5. Garwood, M. and Y. Ke, *Symmetric Pulses to Induce Arbitrary Flip Angles with Compensation for RF Inhomogeneity and Resonance Offsets.* Journal of Magnetic Resonance, 1991(94): p. 511-525.
6. Hu, B. S. and S. M. Conolly, *Method and means for magnetic resonance imaging and spectroscopy using pulsed saturation transfer contrast.* 1993, Google Patents.
7. Hu, B. S., et al., *Pulsed saturation transfer contrast.* Magnetic Resonance in Medicine, 1992. 26(2): p. 231-240.
8. Schneider, E., R. W. Prost, and G. H. Glover, *Pulsed magnetization transfer versus continuous wave irradiation for tissue contrast enhancement.* Journal of Magnetic Resonance Imaging, 1993. 3(2): p. 417-423.
9. Stoeck, C. T., et al., *Optimization of on-resonant magnetization transfer contrast in coronary vein MRI.* Magnetic Resonance in Medicine, 2010. 64(6): p. 1849-1854.
10. Nezafat, R., et al., *Method for spectrally selective B1 insensitive T2 preparation contrast enhancement for high field magnetic resonance imaging.* 2008, Google Patents.
11. Grenier, D., S. Deval, and A. Briguet, *A new approach for on-resonance magnetization transfer parameter optimization.* Magnetic Resonance Materials in Physics, Biology and Medicine, 1998. 7(3): p. 131-140.
12. Pauly, J. M., S. M. Conolly, and D. G. Nishimura, *Magnetic resonance imaging of short T2 species with improved contrast.* 1992, Google Patents.

What is claimed:

1. A magnetic resonance imaging (MM) system comprising:
a signal generator configured to generate a pulse sequence for on-resonance magnetization transfer preparation, the pulse sequence comprising an adiabatic tip-down pulse and a matched adiabatic flip-back pulse for separating spins in a mobile spin pool from spins in a bound spin pool of an anatomical region of interest for imaging, wherein the pulse sequence comprises a time delay between the spatially non-selective adiabatic tip-down pulse and the matched adiabatic spatially non-selective flip-back pulse, and wherein the matched adiabatic flip-back pulse has the time-reversed amplitude modulation function and the time-reversed phase modulation function relative to the respective functions of a tip-down pulse;
a plurality of radio frequency (RF) coils configured to transmit RF pulses in response to the pulse sequence and to acquire RF data in response to transmission of the RF pulses; and
a processing system configured to process the RF data to provide a display image indicating different tissue types with discrimination.

2. A method comprising:
at a magnetic resonance imaging (MM) system:
generating a pulse sequence for on-resonance magnetization transfer preparation, the pulse sequence comprising an adiabatic tip-down pulse and a matched adiabatic flip-back pulse for separating spins in a mobile spin pool from spins in a bound spin pool of an anatomical region of interest for imaging, wherein the pulse sequence comprises a time delay between the spatially non-selective adiabatic tip-down pulse and the matched adiabatic spatially non-selective flip-back pulse, and wherein the matched adiabatic flip-back pulse has the time-reversed amplitude modulation function and the time-reversed phase modulation function relative to the respective functions of a tip-down pulse;
transmitting RF pulses in response to the pulse sequence and to acquire RF data in response to transmission of the RF pulses; and
processing the RF data to provide a display image indicating different tissue types with discrimination.

3. The system of claim 1, wherein the time delay is a first time delay, and wherein the signal generator is configured to produce a second time delay after the flip-back pulse.

4. The system of claim 1, wherein the pulse sequence comprises at least one other set of adiabatic tip-down pulse and a matched adiabatic flip-back pulse.

5. The system of claim 4, wherein the pulse sequence comprises a second time delay between the adiabatic tip-down pulse and the matched adiabatic flip-back pulse in the at least one other set and a third time delay being followed by a gradient pulse for substantially reducing transverse magnetization of the anatomical region of interest.

6. The system of claim 5, wherein said second time delay is zero.

7. The system of claim 1, wherein the pulse sequence for magnetization transfer preparation ends with a second time delay, the second time delay being followed by a gradient pulse for substantially reducing transverse magnetization of the anatomical region of interest.

8. The system of claim 7, wherein the second time delay is zero.

9. The system of claim 1, wherein the tip-down pulse and the flip-back pulse are both adiabatic half passages, and
wherein modulation of the flip-back pulse is a time-mirrored function of the tip-down pulse.

10. The system of claim 1, wherein the tip-down pulse and the flip-back pulse are both adiabatic fast passages, and
wherein the modulation of the flip-back pulse is a time-mirrored function of the tip-down pulse.

11. The system of claim 1, wherein the tip-down pulse and the flip-back pulse are both B1-insensitive pulses with 4 half passages (B1-insensitive rotation, BIR4), and
wherein modulation of the flip-back pulse is a time-mirrored function of the tip-down pulse.

12. The system of claim 1, wherein the tip-down pulse and the flip-back pulse are both tan/tan h modulated pulses, and wherein modulation of the flip-back pulse is a time-mirrored function of the tip-down pulse.

13. The system of claim 1, wherein the tip-down pulse and the flip-back pulse are both FOCI pulses, and
wherein modulation of the flip-back pulse is a time-mirrored function of the tip-down pulse.

14. The system of claim 1, wherein the tip-down pulse and the flip-back pulse are both GOIA pulses, and
wherein modulation of the flip-back pulse is a time-mirrored function of the tip-down pulse.

15. The system of claim 1, wherein the tip-down pulse and the flip-back pulse are both adiabatic half passages, and
wherein modulation of the flip-back pulse is a time-mirrored function of the tip-down pulse.

16. The system of claim 1, wherein the tip-down pulse and the flip-back pulse are both adiabatic fast passages, and
wherein modulation of the flip-back pulse is a time-mirrored function of the tip-down pulse.

17. The system of claim 1, wherein the signal generator is configured to produce a first time delay between the tip-down pulse and the flip-back pulse and a second time delay after the flip-back pulse, and
wherein the first time delay and the second time delay are adaptively selected based on type of tissue or blood discrimination to be performed.

18. The system of claim 1, wherein the adiabatic flip-back and the tip-down pulses have two segments and a last flip-back pulse is replaced with an adiabatic inversion pulse which has four segments, and
wherein the first two segments of said inversion pulse have the time-mirrored modulation functions of the tip-down pulse modulation functions.

19. The system of claim 18, wherein a trailing adiabatic inversion pulse is applied after a gradient pulse for substantially creating inverted magnetization transfer contrast in the anatomical region of interest.

20. The method of claim 2, wherein the time delay is a first time delay, and wherein the signal generator is configured to produce a second time delay after the flip-back pulse.

21. The method of claim 2, wherein the pulse sequence comprises at least one other set of adiabatic tip-down pulse and a matched adiabatic flip-back pulse.

22. The method of claim 21, wherein the pulse sequence comprises a second time delay between the adiabatic tip-down pulse and the matched adiabatic flip-back pulse in the at least one other set and a third time delay being followed by a gradient pulse for substantially reducing transverse magnetization of the anatomical region of interest.

23. The method of claim 22, wherein said second time delay is zero.

24. The method of claim 2, wherein the pulse sequence for magnetization transfer preparation ends with a second time delay, the second time delay being followed by a gradient pulse for substantially reducing transverse magnetization of the anatomical region of interest.

25. The method of claim 24, wherein the second time delay is zero.

26. The method of claim 2, wherein the tip-down pulse and the flip-back pulse are both adiabatic half passages, and
wherein modulation of the flip-back pulse is a time-mirrored function of the tip-down pulse.

27. The method of claim 2, wherein the tip-down pulse and the flip-back pulse are both adiabatic fast passages, and
wherein the modulation of the flip-back pulse is a time-mirrored function of the tip-down pulse.

28. The method of claim 2, wherein the tip-down pulse and the flip-back pulse are both B1-insensitive pulses with 4 half passages (B1-insensitive rotation, BIR4), and
wherein modulation of the flip-back pulse is a time-mirrored function of the tip-down pulse.

29. The method of claim 2, wherein the tip-down pulse and the flip-back pulse are both tan/tan h modulated pulses, and
wherein modulation of the flip-back pulse is a time-mirrored function of the tip-down pulse.

30. The method of claim 2, wherein the tip-down pulse and the flip-back pulse are both FOCI pulses, and
wherein modulation of the flip-back pulse is a time-mirrored function of the tip-down pulse.

31. The method of claim 2, wherein the tip-down pulse and the flip-back pulse are both GOIA pulses, and
wherein modulation of the flip-back pulse is a time-mirrored function of the tip-down pulse.

32. The method of claim 2, wherein the tip-down pulse and the flip-back pulse are both adiabatic half passages, and
wherein modulation of the flip-back pulse is a time-mirrored function of the tip-down pulse.

33. The method of claim 2, wherein the tip-down pulse and the flip-back pulse are both adiabatic fast passages, and
wherein modulation of the flip-back pulse is a time-mirrored function of the tip-down pulse.

34. The method of claim 2, wherein the signal generator is configured to produce a first time delay between the tip-down pulse and the flip-back pulse and a second time delay after the flip-back pulse, and
wherein the first time delay and the second time delay are adaptively selected based on type of tissue or blood discrimination to be performed.

35. The method of claim 2, wherein the adiabatic flip-back and the tip-down pulses have two segments and a last flip-back pulse is replaced with an adiabatic inversion pulse which has four segments, and
wherein the first two segments of said inversion pulse have the time-mirrored modulation functions of the tip-down pulse modulation functions.

36. The method of claim 35, wherein a trailing adiabatic inversion pulse is applied after a gradient pulse for substantially creating inverted magnetization transfer contrast in the anatomical region of interest.

* * * * *